(12) United States Patent
Movshovich (10) Patent No.: US 12,109,148 B1
(45) Date of Patent: Oct. 8, 2024

(54) CORNEAL IRRIGATION SYSTEM AND METHOD OF USE

(71) Applicant: Alexander Ilich Movshovich, New York, NY (US)

(72) Inventor: Alexander Ilich Movshovich, New York, NY (US)

( * ) Notice: Subject to any disclaimer, the term of this patent is extended or adjusted under 35 U.S.C. 154(b) by 0 days.

(21) Appl. No.: 18/603,461

(22) Filed: Mar. 13, 2024

(51) Int. Cl.
- *A61F 9/007* (2006.01)
- *A61F 9/00* (2006.01)
- *A61M 5/315* (2006.01)

(52) U.S. Cl.
CPC ........ *A61F 9/00709* (2013.01); *A61F 9/0017* (2013.01); *A61M 5/31513* (2013.01); *A61M 2210/0612* (2013.01)

(58) Field of Classification Search
CPC ................ A61F 9/0017; A61F 9/00709; A61F 9/00736; A61F 9/00754; A61F 9/00745; A61F 9/00763; A61M 25/007; A61B 2017/320044
See application file for complete search history.

(56) References Cited

U.S. PATENT DOCUMENTS

| | | |
|---|---|---|
| 772,266 A | 10/1904 | Alley |
| 5,203,865 A | 4/1993 | Siepser |
| 5,258,002 A | 11/1993 | Jeffers |
| 5,370,652 A | 12/1994 | Kellan |
| 5,607,437 A | 3/1997 | Simon |
| 5,653,725 A | 8/1997 | Simon |
| 7,722,669 B2 | 5/2010 | Foulkes |
| 2002/0055753 A1* | 5/2002 | Silvestrini ............... A61F 2/148 606/166 |
| 2010/0280535 A1 | 11/2010 | Yamaguchi |
| 2013/0231605 A1* | 9/2013 | Walter ................ A61F 9/00745 604/27 |
| 2014/0107631 A1 | 4/2014 | Ferrari |
| 2015/0305927 A1 | 10/2015 | Walter |
| 2020/0046560 A1* | 2/2020 | Thyzel ................ A61F 9/00804 |

FOREIGN PATENT DOCUMENTS

WO   2018122537 A1   7/2018

OTHER PUBLICATIONS

A photograph of Capsule Polisher-Kratz, 21G (.80mm) 4 mm Top Port product available from Hurricane Medical, Bradenton, FL USA, prior to Mar. 13, 2024. (1 page).

(Continued)

*Primary Examiner* — Scott J Medway
*Assistant Examiner* — Anh Bui
(74) *Attorney, Agent, or Firm* — Koffsky Schwalb LLC (57) ABSTRACT

A corneal irrigation system, for removing a color pigment(s) from an intracorneal channel, includes a syringe, an irrigation device, and a flexible tube coupling the syringe to the irrigation device. The irrigation device includes a handle, having a distal end and a proximal end, that is coupled to the cannula. The handle also includes a lumen. The cannula includes (i) a shaft section having a first end that is coupled to the handle's proximal end, (ii) a curved section having a blunt tip, wherein an exterior surface of the curved section includes a rough-surface region, and (iii) a lumen having an opening in the rough-surface region, the lumen extending from the first end of the shaft section toward the blunt tip. The cannula's lumen is coupled to the handle's lumen.

6 Claims, 11 Drawing Sheets

(56) References Cited

OTHER PUBLICATIONS

Alió, Jorge L., et al. "Femtosecond-assisted keratopigmentation for functional and cosmetic restoration in essential iris atrophy." Journal of Cataract & Refractive Surgery 37.10 (2011): 1744-1747.

Alió, Jorge L., et al. "Keratopigmentation to change the apparent color of the human eye: a novel indication for corneal tattooing." Cornea 35.4 (2016): 431-437.

D'Oria, Francesco, Sabat K. Abu-Mustafa, and Jorge L. Alio. "Cosmetic change of the apparent color of the eye: a review on surgical alternatives, outcomes and complications." Ophthalmology and Therapy 11.2 (2022): 465-477. Printout from https://link.springer.com.

Hasani, Hamidreza, et al. "Keratopigmentation: a comprehensive review." Eye 34.6 (2020): 1039-1046. Pintout from www.https://nature.com.

\* cited by examiner

CORNEAL IRRIGATION SYSTEM AND METHOD OF USE

FIELD OF THE INVENTION

This invention relates to a field of ophthalmology.

BACKGROUND OF THE INVENTION

Keratopigmentation is a procedure involving the placement of the pigment inside of the cornea. The procedure has gained popularity as a means to alter the appearance of the eye. However, in cases where the intended aesthetic has not been achieved and alteration of the previously placed pigment is desired, reversing the effect of keratopigmentation presents challenges.

Reversing the keratopigmentation procedure or re-adjusting the appearance of eye color or its intensity by existing techniques, often requires complex invasive procedures with associated risks. Therefore, there is a need for a safe and effective system and method for removal of the placed pigment specifically designed for patients who have undergone keratopigmentation.

By using a corneal irrigation system and method (depigmentation procedure) of the present invention, the effect of the prior keratopigmentation procedure can be reversed in a safe and effective manner.

SUMMARY OF THE INVENTION

The present invention introduces a method and a device for corneal depigmentation following the keratopigmentation procedure, employing a combination of liquid solution used for irrigation of an intracorneal channel and a targeted irrigation device, which is a part of the corneal irrigation system of the present invention.

The invented procedure begins with opening one or more existing radial incisions in the cornea from the front of the eye, to reach the intracorneal channel initially formed during a prior keratopigmentation procedure. In cases where there are two radial incisions, also initially made during the prior keratopigmentation procedure, preferably both incisions are opened. The radial incision(s) may be opened using an ophthalmological spatula.

Next, the tip of the irrigation device's cannula, the cannula specifically designed to include a rough-surface region and a lumen opening, is inserted into the intracorneal channel via one of the opened radial incisions. (As used herein, the term "lumen" refers to an inner space in tubes that can transport liquids, gases, or surgical devices during a medical procedure.) At this time, at least a portion of the rough-surface region of the cannula is moved or rotated within the intracorneal channel back and forth. By moving or rotating the rough-surface region of the cannula within the intracorneal channel back and forth, one scrubs and detaches the color pigments, injected into the cornea during the prior keratopigmentation procedure, from walls of the intracorneal channel.

Finally, either while scrubbing the walls of the intracorneal channel or following the scrubbing step, an irrigation fluid (liquid) is injected into the intracorneal channel through the cannula's lumen opening, to flush out the detached color pigments from the intracorneal channel, via one or more opened radial incisions. In addition, any previously unattached pigment that might have been present in the intracorneal channel would also get flushed out. In one embodiment of the invention, the irrigation fluid is a balanced salt solution.

Unlike the existing techniques, the proposed depigmentation procedure is minimally invasive. Furthermore, the method offers precise control over the extent and duration of cornea depigmentation, enabling customizable outcomes tailored to individual preferences.

As a result, the invention represents a significant advancement in ophthalmic aesthetics, presenting a safe and effective solution for cornea depigmentation after keratopigmentation with broad applicability and favorable outcomes.

In one embodiment of the invented corneal irrigation system for removing a color pigment(s) from an intracorneal channel includes a syringe, a hand-held device, and a flexible tube coupling the syringe to the hand-held device. The syringe includes a barrel for holding an irrigation fluid, the barrel having a distal opening at one end and a fluid port at the other end. The syringe also includes a plunger configured to be inserted into the distal opening of the barrel and further configured to slide within the barrel.

The hand-held device includes a handle that is coupled to a specially designed cannula. The handle has a distal end and a proximal end. The handle also includes a lumen (handle's lumen). In one embodiment, the handle's lumen extends from the handle's distal end to the handle's proximal end.

The cannula includes (i) a shaft section having a first end that is coupled to the handle's proximal end, (ii) a curved (arcuate) section having a blunt tip, wherein an exterior surface of the curved section includes a rough-surface region that, preferably, encompasses the blunt tip, and (iii) a lumen (cannula's lumen) having an opening in the rough-surface region of the curved section and extending from the first end of the shaft section toward the blunt tip of the curved section. The cannula's lumen is coupled to the handle's lumen.

The flexible tube has a first end and a second end, the first end of the tube configured for coupling the tube to the fluid port of the barrel and the second end of the tube is configured for coupling the tube to the handle's lumen at the handle's distal end.

In one embodiment, the rough-surface region has a cross-section that matches the intracorneal channel. The cross-section may vary along the length of the rough-surface region.

In one embodiment, the curved section extends in a plane that forms an angle with a shaft-axis of the shaft section.

In one embodiment, the cannula further includes an intermediate section extending between the shaft section and the curved section, an axis of the intermediate section being nonparallel with the shaft-axis of the shaft section.

In one embodiment, the opening of cannula's lumen includes a plurality of openings distributed along the rough-surface region of the curved section.

In one embodiment, the method for irrigating an intracorneal channel uses a hand-held irrigation device that includes a cannula. The cannula comprises (i) a shaft section having a first end, (ii) a curved section having a blunt tip, wherein an exterior surface of the curved section includes a rough-surface region that, preferably, encompasses the blunt tip, and (iii) a lumen extending from the first end of the shaft section toward the blunt tip of the curved section, the lumen including an opening in the rough-surface region of the curved section.

The method includes the steps of: (a) opening a radial incision of a plurality of radial incisions, (b) inserting a part of the rough-surface region of the curved section into the intracorneal channel via the opened radial incision; (c)

moving, preferably back and forth, the inserted part of the rough surface region of the curved section within the intracorneal channel, to detach color pigment(s) from a wall(s) of the intracorneal channel; (d) injecting an irrigation fluid into the intracorneal channel through the lumen opening(s) in the rough-surface region of the curved section, to flush the detached color pigment(s) from the intracorneal channel, via one or more radial incisions that have been opened. As used herein, the phrase "inserting a part of the rough-surface region" refers to inserting any portion of the rough-surface region, up to and including 1000% of the rough-surface region.

In one embodiment, the step of opening the radial incision may be performed using a spatula.

In one embodiment, the injecting step may be performed simultaneously with the moving step. In another embodiment, the injecting step may be performed following the moving step.

BRIEF DESCRIPTION OF THE DRAWINGS

The accompanying figures, where like reference numerals refer to identical or functionally similar elements throughout the separate views, together with the detailed description below, are incorporated in, form part of the specification, and serve to further illustrate embodiments of concepts that include the claimed invention and explain various principles and advantages of those embodiments.

Skilled artisans will appreciate that elements in the figures, which form a part of this disclosure, are illustrated for simplicity and clarity and have not necessarily been drawn to scale. For example, the dimensions of some of the elements in the figures may be exaggerated relative to other elements to help improve understanding of embodiments of the present invention.

DETAILED DESCRIPTION OF THE INVENTION

The following detailed description discloses several embodiments of the system and method of the present invention.

The invention is directed at a corneal irrigation system and a depigmentation procedure in which an irrigation device is used to remove color pigments from an intracorneal channel, formed in the cornea during a keratopigmentation procedure.

The keratopigmentation procedure or corneal tattooing, is a specialized surgical procedure that involves the application of pigment to the cornea, that covers a person's natural color of iris, allowing individuals to modify and enhance their eyes color when viewed from the front.

In some instances, patients may wish to reverse the keratopigmentation procedure or re-adjust the appearance of their eyes color or its intensity. By using a corneal irrigation system and method (depigmentation procedure) of the present invention, some or substantially all of previously introduced color pigment could be removed from the cornea.

Figure 1A:
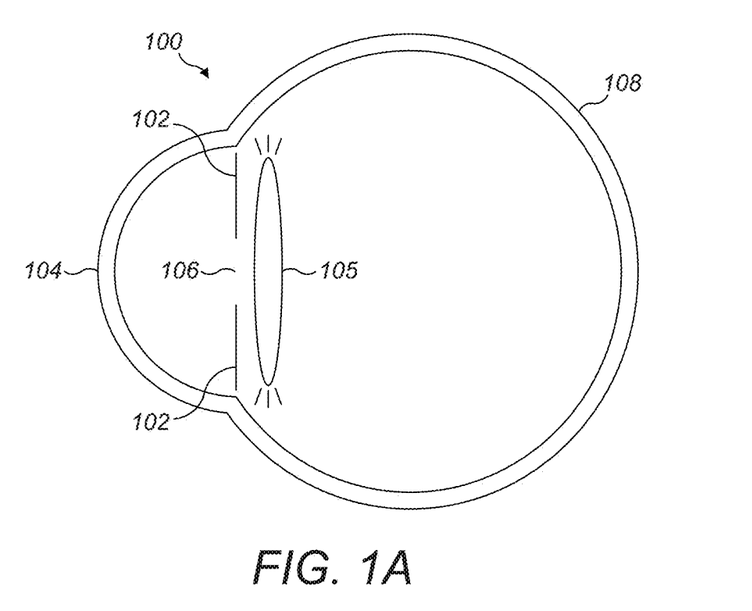
FIGS. 1A and 1B illustrate cross-sectional view and front view, respectively, of human eye.
Figure 1B:
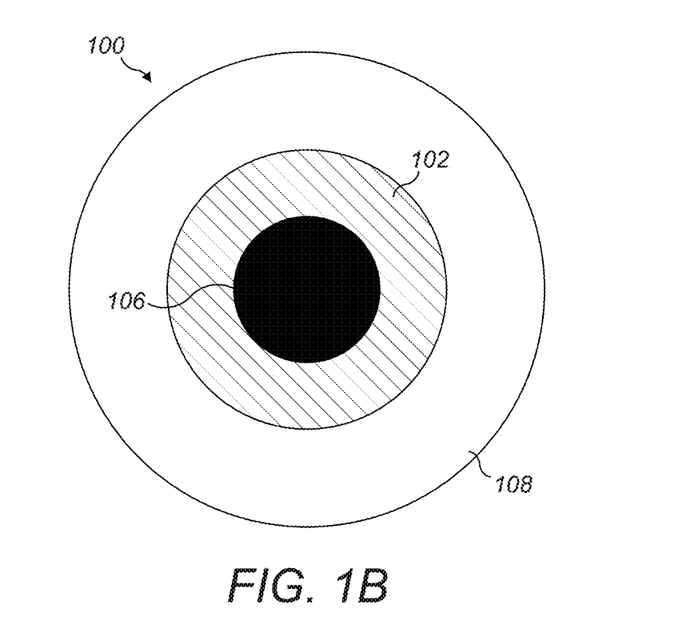

FIGS. 1A and 1B show a cross-sectional and a front view, respectively, of a human eye 100. This is the state before the eye's color has been modified by the keratopigmentation procedure. It should be noted that, because the human eye is not perfectly spherical or symmetrical, the two figures are intended for explanatory purposes only.

As shown in FIG. 1A, eye 100 includes cornea 104, which is a clear layer forming the front portion of the eye that allows light to pass into the eye. Continuous with cornea 104 is sclera 108, which is the w % bite outer coating of the eye 100. Sclera is tough, fibrous tissue that extends from the cornea 104 to the optic nerve at the back of the eye 100.

FIG. 1A also shows iris 102, which is a thin annular structure located behind the cornea 104 and which determines the eye's natural color. The opening in the center of iris 102 is called pupil 106. The pupil's size is adjusted by the iris 102 to control the amount of light that enters the eye. The iris 102 may dilate (become larger) or contract (become smaller) depending on the changes in ambient lighting conditions, such that the pupil 106 may dilate at low lighting level or contract at high lighting level. Positioned behind iris 102 is lens 105, which focuses the incoming light onto the light-sensitive cells in the back of the eye. These light-sensitive cells are collectively referred to as retina.

FIG. 1B depicts the eye 100 of FIG. 1A when viewed from the front. As such, FIG. 1B shows iris 102 and pupil 106 surrounded by sclera 108. Because the light entering the eye through the pupil does not get reflected back, when viewed from the front, the pupil always appears black.

Figure 2A:
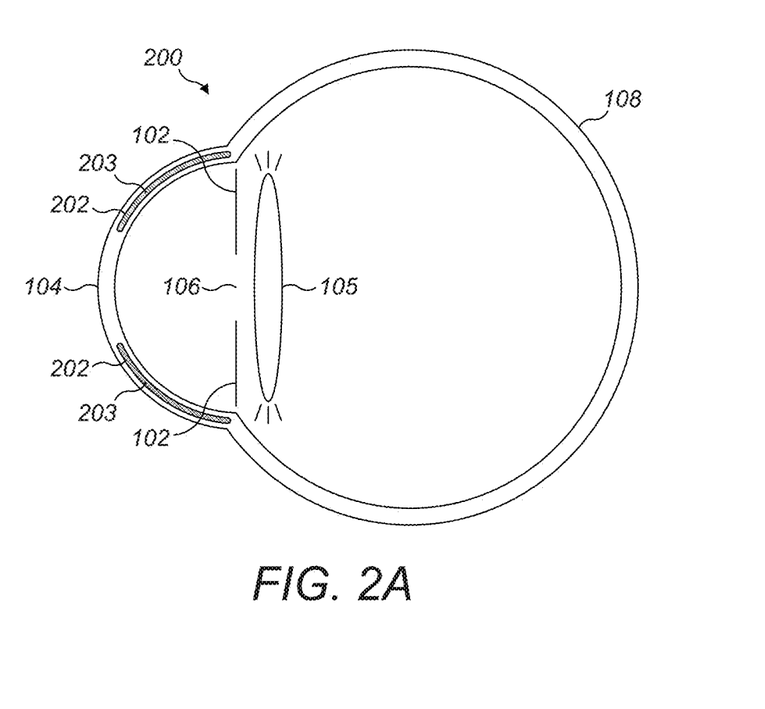
FIGS. 2A and 2B illustrate cross-sectional view and front view, respectively, of human eye after a keratopigmentation procedure.
Figure 2B:
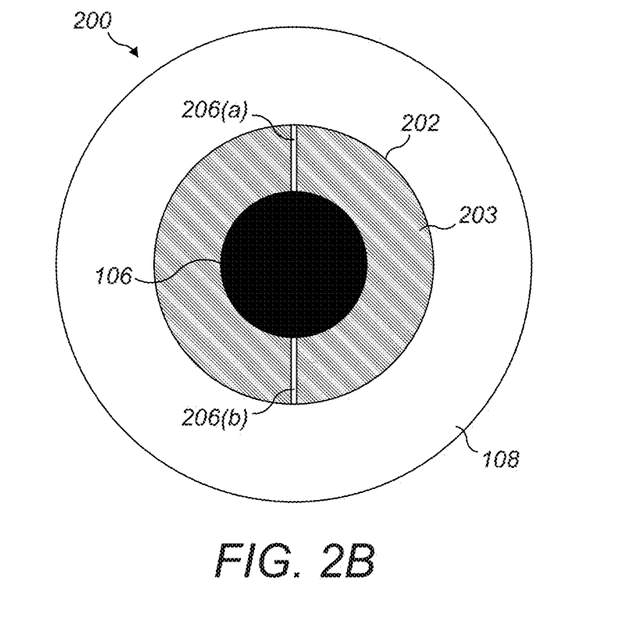

FIGS. 2A and 2B present a cross-sectional view and a front view respectively, of a human eye 200 after a known color pigmentation procedure—keratopigmentation. The keratopigmentation procedure involves forming an intracorneal channel 202 inside the cornea 104, making two radial incisions (206(a) and 206(b) in FIG. 2B) from the front of the eye, to reach the intracorneal channel 202, and injecting a color pigment 203 into the intracorneal channel 202 through one or both radial incisions. When the eye 200 is viewed in cross-section, FIG. 2A, cornea 104 now includes an intracorneal channel 202 with color pigments 203 in it. When viewed from the front, as shown in FIG. 2B, eye 200 includes radial incisions 206(a) and 206(b) and the intracorneal channel 202 with color pigments 203 in it. To prevent color pigments 203 from blocking the light entering the pupil, the size and shape of the intracorneal channel is made to cover the iris 102 when the pupil is large (dilated), which is the situation depicted in FIG. 2B. As a result, the injected color pigments 203 substantially or completely cover (overlay) the natural color of the iris 102, and the eye 200 appear to have the color of the injected color pigments 203.

Figure 3:
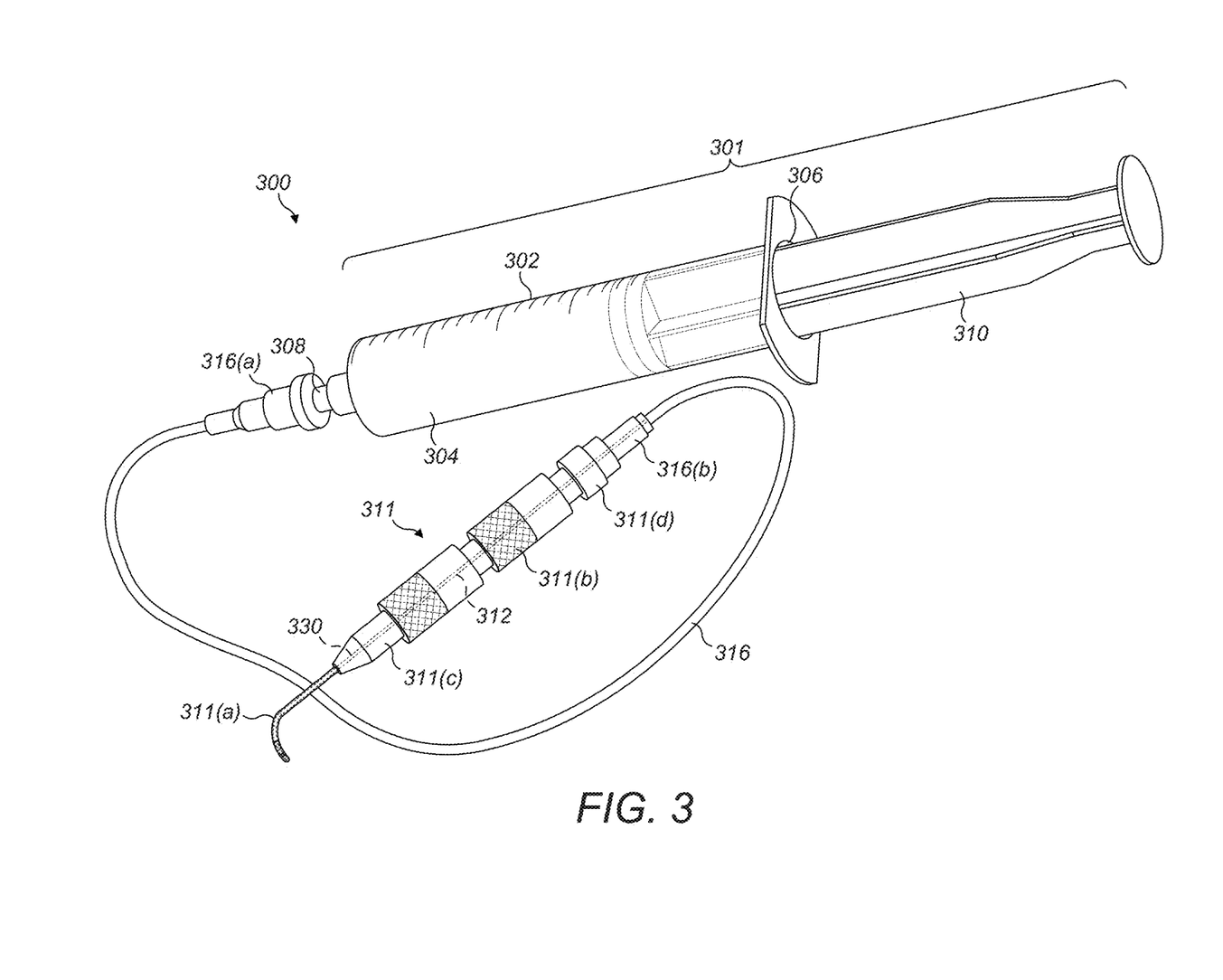
FIG. 3 shows corneal irrigation system according to an embodiment of the present invention.

FIG. 3 shows a corneal irrigation system 300 for irrigating and/or removing the color pigment 203 from the intracorneal channel 202 of the human eye 200 in FIGS. 2A and 2B. The system 300 includes a syringe 301, a hand-held irrigation device 311, and a flexible tube 316 coupling the syringe 301 to the irrigation device 311.

The syringe 301 includes a barrel 302 designed to hold an irrigation fluid 304 which is used in the invented depigmentation process to remove and wash out from the intracorneal channel the previously injected pigment 203. The barrel 302 includes a distal opening 306 and a fluid port 308 at the syringe's proximal end.

The syringe 301 further includes a plunger 310 designed and constructed to be inserted into the distal opening 306. The plunger 310 is configured to be able to slide back and force within the barrel 302. The plunger 310 can be pushed or pulled to create a force that either sucks the irrigation fluid 304 into the syringe or pushes it out of the syringe 301. For example, pushing the plunger 310 into the barrel 302, forces the irrigation fluid 304 to be pushed out of the fluid port 308 at the proximal end of the syringe. Conversely, pulling the plunger 310 back creates a vacuum in the barrel 302, which in turn causes the fluid 304 to be sucked into the syringe 301 through the fluid port 30g. The site of the barrel 302 and the force applied to the plunger 310 determine the amount of fluid 304 that can be sucked into or pushed out of the syringe.

The hand-held irrigation device 311 is used for scrubbing interior surfaces of the intracorneal channel 202, to detach from it any color pigments, for irrigating the channel, and for removing color pigments from the channel. The irrigation device 311 includes a cannula 311(a), which includes a cannula's lumen 330, that is coupled to a handle 311(b), which also includes a handle's lumen 312.

The handle 311(b) includes a proximal end 311(c) and a distal end 311(d). The handle's lumen 312 extends from the handle's proximal end 311(c) to its distal end 311(d).

The cannula 311(a) is mechanically coupled to the handle 311(b), leading the handle's lumen 312 to be coupled to the cannula's lumen 330 of the cannula 311(a), which allows the irrigation fluid 304 to pass through the irrigation device 311.

The flexible tube 316 is configured to have its first end 316(a) coupled to the syringe's 301 fluid port 308 and to have its second end 316(b) coupled to the irrigation device's 311 distal port 311(d). In another embodiment, when a handle does not include a lumen, the second end 316(b) of the flexible tube 316 may be directly coupled to the cannula's lumen 312.

As mentioned above, when the plunger 310 is pulled toward the distal opening 306, it creates a vacuum in the barrel 302, allowing the irrigation fluid 304 to be sucked in from an external fluid-supply source and filling the barrel 302 to a predetermined level. Then, when the plunger 310 is pushed towards the fluid port 308, it pushes the irrigation fluid 304 out of the barrel 302 through the fluid port 308. When the elements are connected as shown in FIG. 3, with the irrigation fluid 304 in the barrel 302, pushing the plunger 310 toward the fluid port forces the fluid to flow out of the barrel 302 and into the first end 316(a) of the flexible tube 316, to flow through the flexible tube 316, and to exit through the second end 316(b) of the flexible tube 316 into the lumen 312 of the handle of irrigation device 311. The irrigation fluid 304 then flows through the lumen 312 of the handle 311(b) and, at the handle's proximal end 311(c), enters the lumen 330 of the cannula 311(a). Finally, as explained in more detail below, the fluid 304 is ejected from the lumen 330 of cannula 311(a) through an opening in the lumen.

Figure 4A:
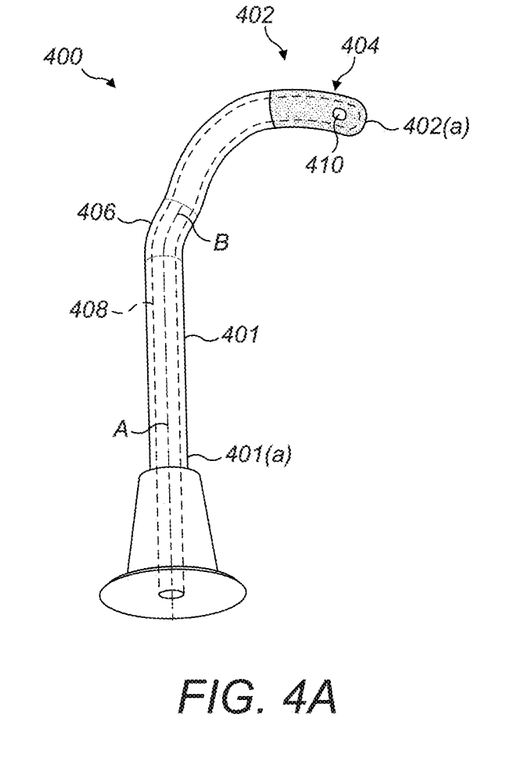
FIGS. 4A and 4B show perspective views of cannula of the corneal irrigation system according to an embodiment of the present invention.
Figure 4B:
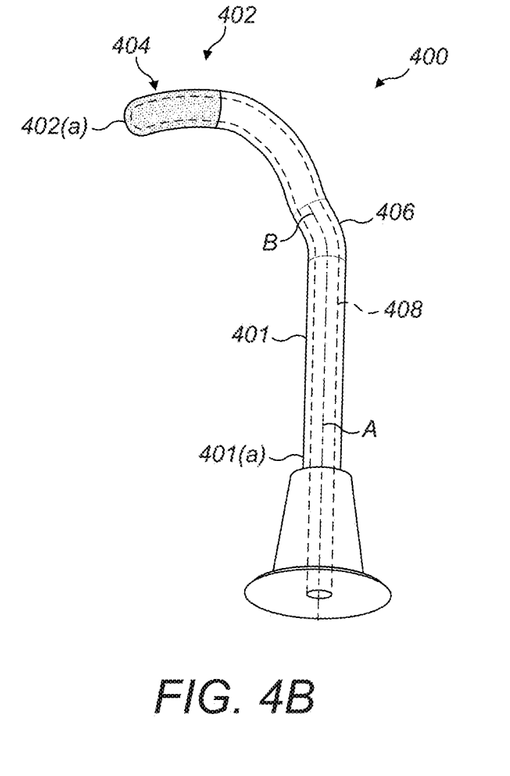
Figure 4C:
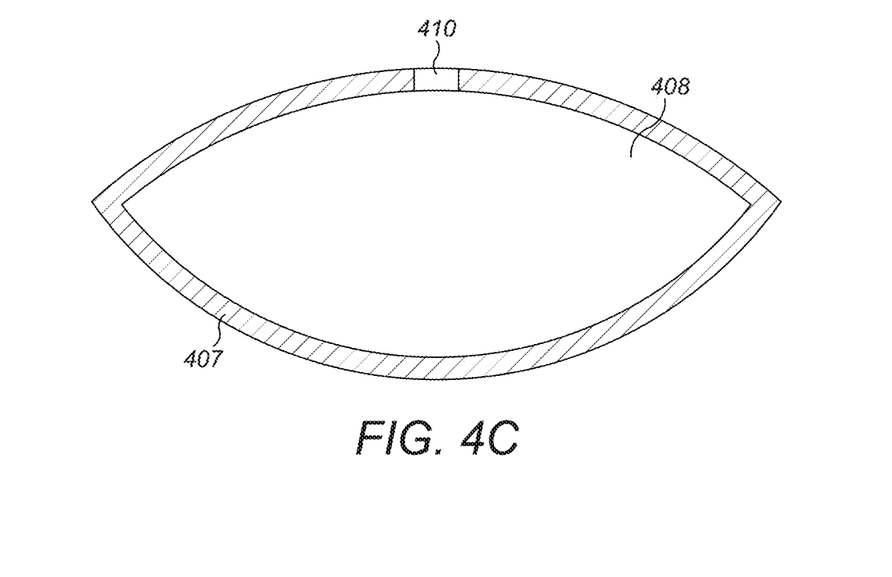
FIG. 4C shows a cross-sectional view of the cannula in FIGS. 4A and 4B along a lumen opening according to an embodiment of the present invention.

FIGS. 4A, 4B and 4C show the various elements and additional views of the cannula 400, previously designated by reference 311(a) in FIG. 3. Specifically, FIG. 4B shows the reverse side of the cannula 400 in FIG. 4A, while FIG. 4C shows a cross-section of the cannula 400.

The cannula 400 shown in FIG. 4A includes a shaft section 401, a curved section 402, and an intermediate section 406 coupling the shaft and curved sections. The shaft section 401 has a first end 401(a), which can be considered one end of the cannula. The shaft section 401 has an axis (reference "A" in FIGS. 4A and 4B) that runs at an angle to the axis of (reference "B" in FIGS. 4A and 4B) the intermediate section 406, so that the two axes are not parallel. In one preferred embodiment, the curved section 402 runs in a plane that is at an angle to the shaft section's axis A and, preferably, to the intermediate section's axis B.

The curved section 402 has a blunt tip 402(a), which forms the other end of the cannula. The exterior surface of the curved section 402 includes a rough-surface region 404. Lumen 408 of the cannula 400 extends from the first end of 401(a) of the shaft section 401 to an opening 410 in the rough-surface region 404. In one embodiment of the invention, as shown in FIG. 4A, the opening 410 is located near the blunt tip 402(a). In another embodiment of the invention, the opening 410 may be located at the blunt tip 402(a).

In one embodiment, the rough-surface region 404 encompasses the blunt tip 402(a) of the cannula 400, to ease the process of scrubbing the walls of intracorneal channel 202, effectively detaching the previously deposited color pigment 203. In another embodiment, the rough-surface region 404 does not encompass the blunt tip 402(a) of the cannula 400 but stops before it.

The rough-surface region 404 can be implemented by various techniques. In one embodiment of this invention, the rough-surface region 404 can be created by plating diamond particles, dust, or powder onto the exterior surface of the cannula's curved section 402. In another embodiment, the rough-surface region can be created by scratching the exterior surface of the cannula. In yet another embodiment, the rough-surface region could be formed during molding of the cannula.

According to one embodiment of the invention, the rough-surface region 404 of the cannula 400 has a cross-sectional shape shown in FIG. 4C. The figure shows a cannula wall 407 (preferably metallic) with the lumen 408 on the inside and the lumen opening 410 through the wall 407. In one embodiment of the invention, as shown in FIG. 4C, the exterior surface of the wall 407 is made pointy on both sides (edges), to substantially match the geometry of the intracorneal channel 202 when the cannula is inserted into the channel. This allows the rough-surface region 404 of the cannula 400 to reach and detach color pigments along the edges of the intracorneal channel.

In another embodiment, the exterior surface of the wall 407 is made with non-pointy sides.

While in the embodiment depicted in FIGS. 4A and 4B, the cross-section of the rough-surface region 404 does not change, such a cross-section, in fact, any cross-section of any region of the curved section, may vary along the length of such region. For example, the curved section may either widen toward the blunt tip 402(a) or it may narrow. Similarly, the cross-sectional height may increase toward the blunt tip 402(a) or it may decrease.

FIG. 4B shows one an embodiment of the other (back) side of the cannula 400 in FIG. 4A. Specifically, the other side of the rough-surface region 404 in FIG. 4B does not include any limen openings.

Figure 5:
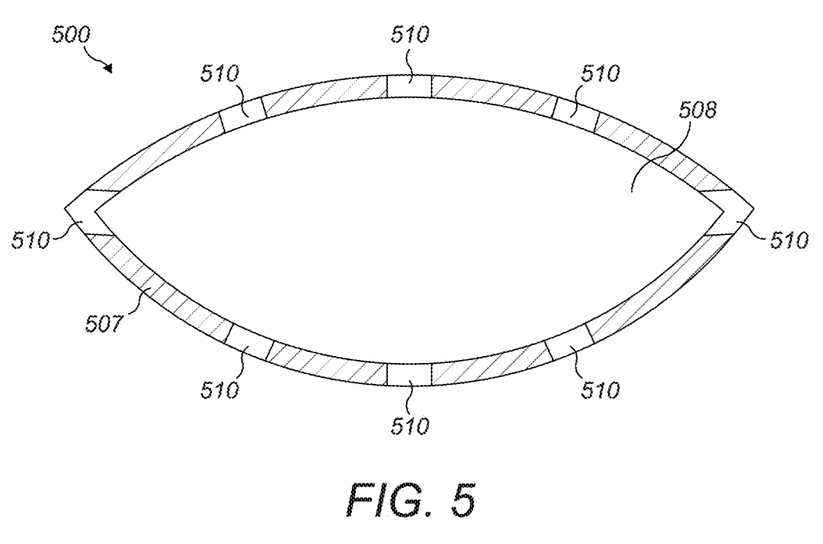
FIG. 5 shows a cross-sectional view of another embodiment of cannula of the present invention.

FIG. 5 shows a cross-section of yet another embodiment of the cannula of the present invention. The cannula 500 in FIG. 5 has a cross-section similar to the one in FIG. 4C, except that in FIG. 5 the cannular wall 507 includes many lumen openings, represented by multiple references 510, with at least one of these openings being located in the rough-surface region of the cannula's curved section.

In one embodiment, all of the openings are located in the same cross-sectional plane, while in another embodiment the some of the openings may be located in different cross-sectional planes.

Figure 6A:
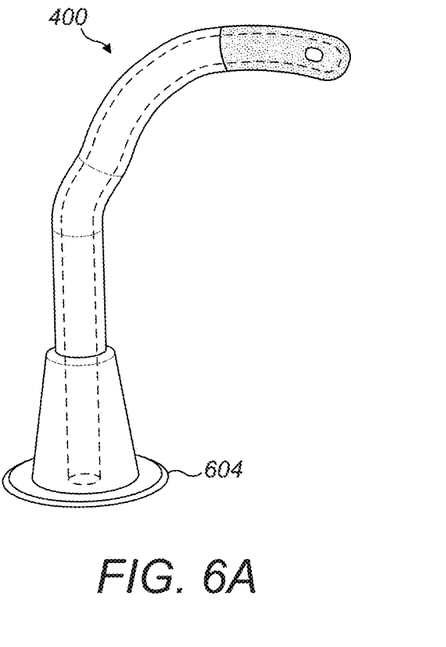
FIGS. 6A and 6B illustrate a pair of complementary cannulas according to an embodiment of the present invention.

FIG. 6A presents another view of the irrigation device 311 of the corneal irrigation system 300 in FIG. 3. Here, the cannula 400 is coupled to the proximal end 604 of the handle of the irrigation device, referenced in FIG. 3 as the proximal end 311(c) of the handle 311(b) of the irrigation device 311.

Figure 6B:
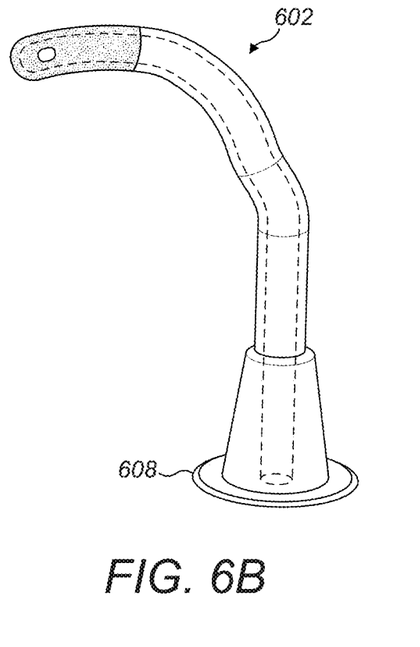

FIG. 6B demonstrates yet another embodiment of the irrigation device of present invention. FIG. 6B shows an irrigation device whose cannula design is complementary to the cannula in the irrigation device of FIG. 6A. Specifically, the cannula 602 in FIG. 6B is configured as a mirror image of the cannula 400 in FIG. 6A.

In one method of the present invention, the irrigation device shown in FIG. 6A could be used to enter the intracorneal channel 202 (FIG. 2A) through the radial incision 206(a) from the left to the right, rotated in clockwise fashion and shifted through the channel back and forth. Alternatively, the irrigation device shown in FIG. 6A could be used to enter the intracorneal channel 202 through the radial incision 206(b) from the right to the left, rotated in clockwise fashion and shifted through the channel back and forth. Conversely, the irrigation device shown in FIG. 6B could be used to enter the intracorneal channel 202 through the radial incision 206(a) from right to left, rotated counterclockwise and shifted through the intracorneal channel 202 back and forth. Alternatively, the irrigation device shown in FIG. 6B could be used to enter the intracorneal channel 202 through the radial incision 206(b) from the left to the right, rotated in counterclockwise fashion and shifted through the intracorneal channel 202 back and forth.

Figure 7:
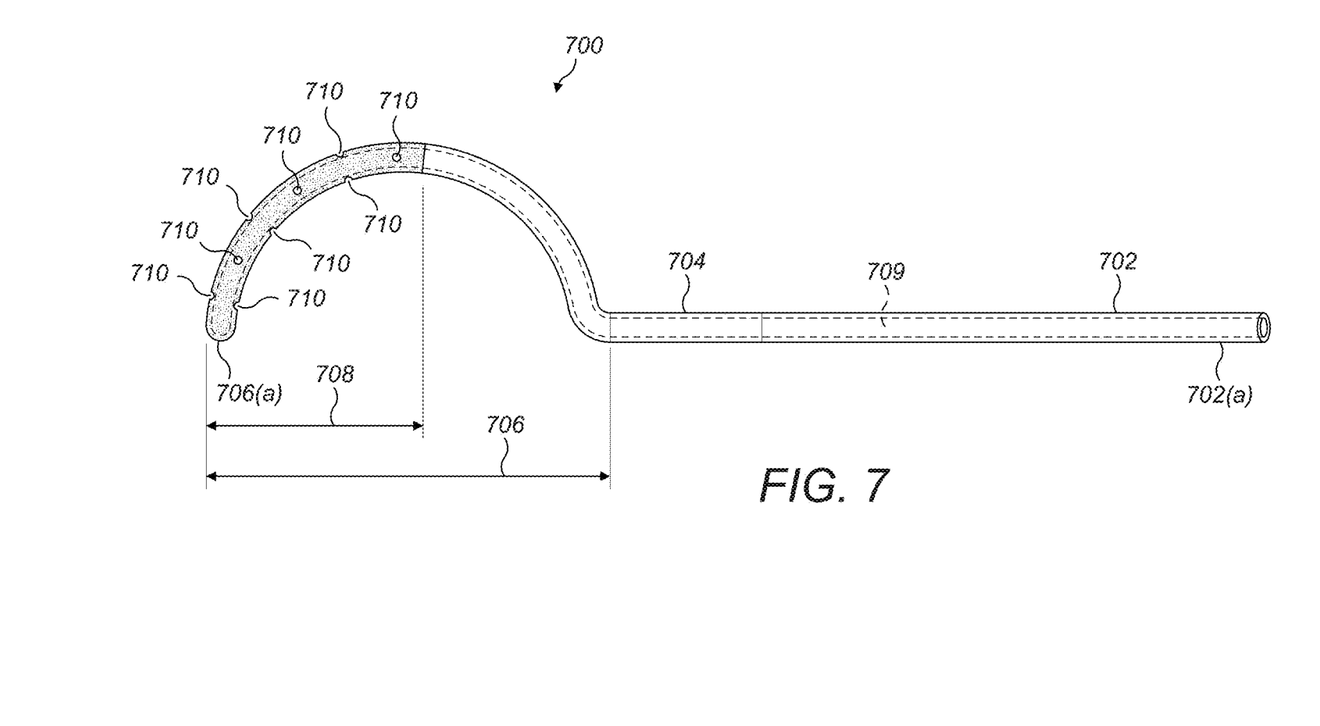
FIG. 7 illustrates an alternate embodiment of cannula of the present invention.

FIG. 7 demonstrates yet another embodiment of the cannula of the present invention. Specifically, a cannula 70) includes a shaft section 702, an intermediate section 704, a curved section 706, and a lumen 709 passing through each of the sections. The shaft section 702 further contains a first end 702(a). The curved section 706 further includes a blunt tip 706(a), a rough-surface region 708, and a plurality of lumen openings 710 distributed along the rough-surface region 708 of the curved section 706. The plurality of lumen openings allows an operator to achieve a more effective irrigation of the intracorneal channel 202 (FIG. 2A) leading to a quicker, more effective removal of the color pigments 203.

Figure 8A:
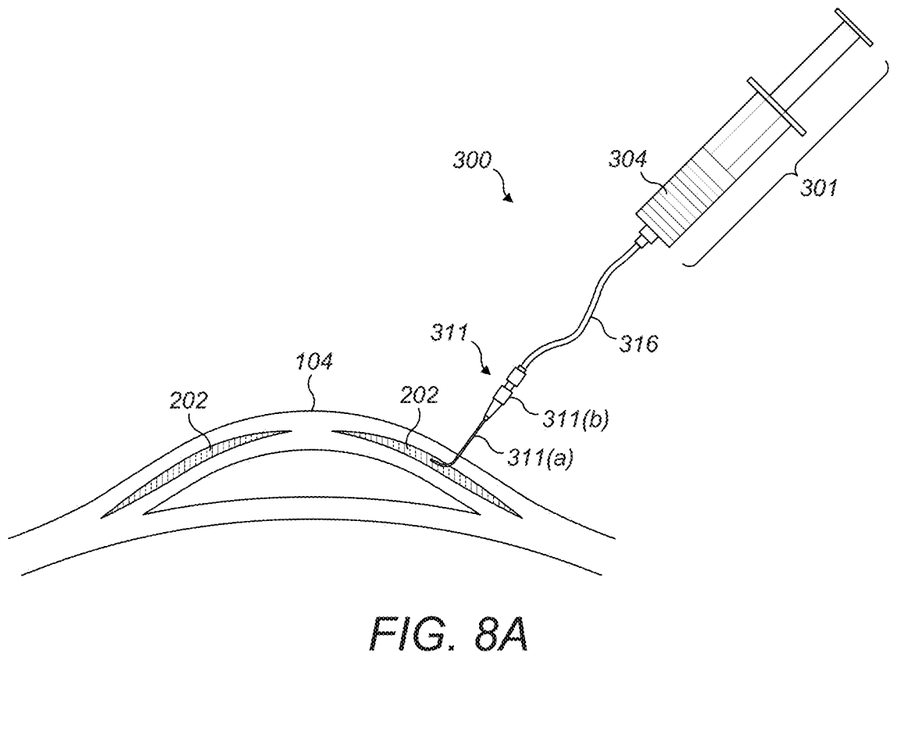
FIG. 8A depicts the corneal irrigation system of FIG. 3 during a depigmentation procedure of the present invention.
Figure 8B:
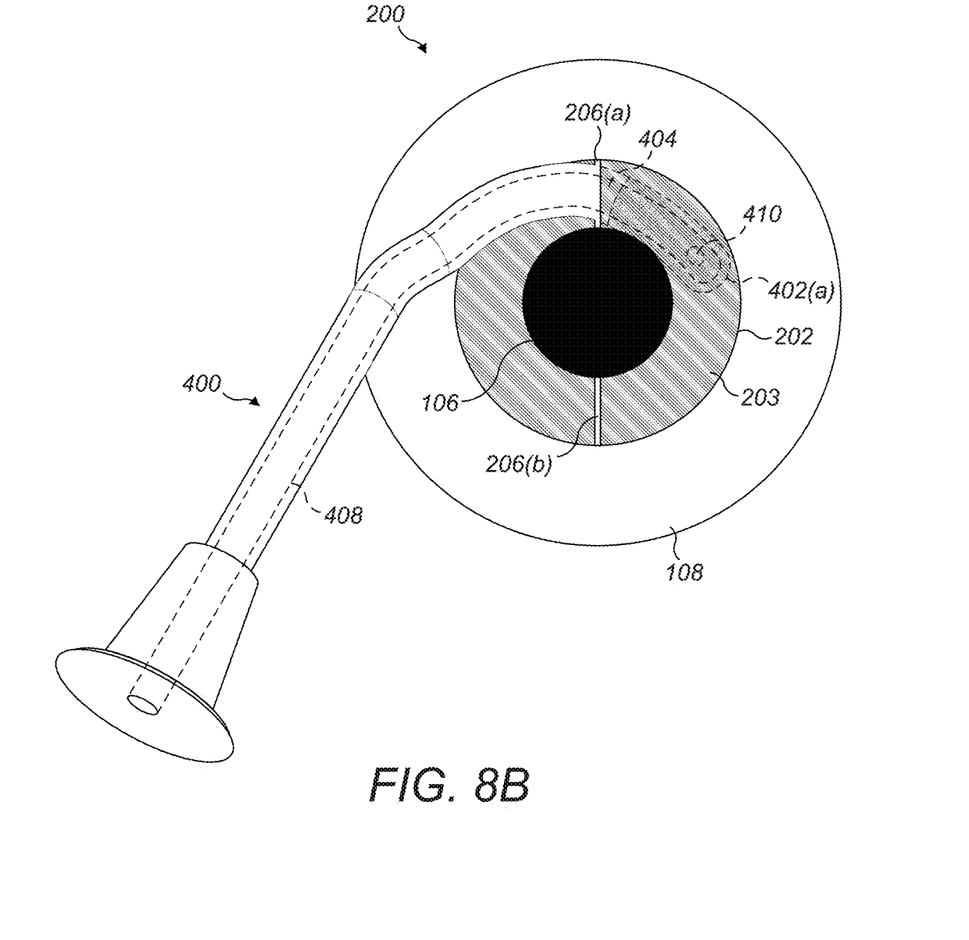
FIG. 8B provides a detailed view of the cannula in FIG. 8A.

FIG. 8A depicts the corneal irrigation system during a depigmentation procedure of the present invention, and FIG. 8B provides a detailed view of the cannula in FIG. 8A. As a result, FIGS. 8A and 8B collectively illustrate the corneal irrigation system, with a cannula of the system's irrigation device, during a depigmentation procedure of the present invention.

Specifically, FIG. 8A shows the corneal irrigation system 300 in operation, where the cannula 311(a) is already inserted into the intracorneal channel 202. FIG. 8A also shows the syringe 301 filled with the irrigation fluid 304, where syringe 301 is coupled with the irrigation device 311 through the flexible tube 316, so that, when one is pushing the syringe plunger 310 (see FIG. 3), the irrigation fluid 304 can travel from the syringe 301 through the flexible tube 316, then through the lumen 312 of the handle 311(b) and then through the lumen 408 of the cannula 400, referenced in FIG. 8A as 311(a), into the intracorneal channel 202.

FIG. 8B shows a more detailed view of the cannula of the invented depigmentation corneal irrigation system 300 in operation, presenting a front view of a human eye 200 that previously underwent the keratopigmentation procedure. FIG. 8B shows the cannula 400 inserted into the intracorneal channel 202 through the radial incision 206(a). FIG. 8B further shows the eye's pupil 106, the sclera 108, the cannula's lumen 408 and the lumen opening 410. Finally, FIG. 8B shows the color pigment 203 previously deposited into the intracorneal channel 202 during the keratopigmentation procedure.

By inserting the blunt tip 402(a) of the cannula's curved section 402 into the intracorneal channel 202 via one of the radial incisions and then moving or rotating the cannula within the intracorneal channel 202 back and forth, one can scrub and detach the color pigment 203 from walls of the intracorneal channel 202. Furthermore, while scrubbing walls of the intracorneal channel 202 or following a scrubbing step, one can inject the irrigation fluid 304 into the intracorneal channel 202 to flush out the detached color pigments from the intracorneal channel 202 via radial incisions 206(b) and 206(a). In some cases, the radial incision 206(a) should be opened using a spatula before inserting a cannula's blunt tip 402(a) into the intracorneal channel 202.

Figure 9:
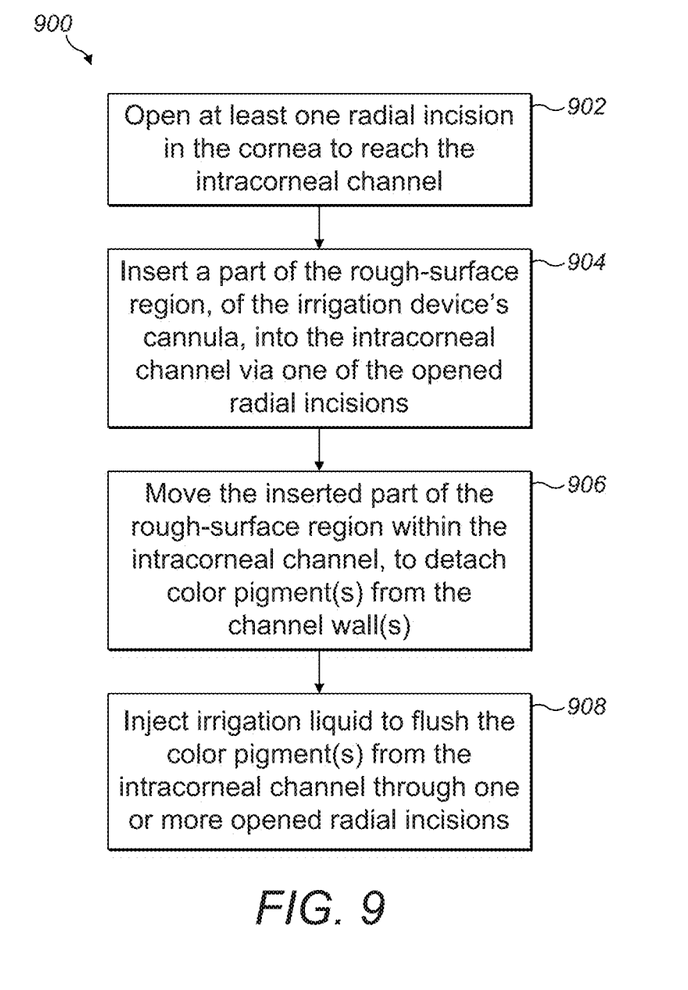
FIG. 9 is a flowchart depicting the depigmentation procedure according to an embodiment of the present invention.

FIG. 9 shows a depigmentation procedure (method) 900 according to one embodiment of the present invention. Looking at FIG. 9, the method starts at Step 902 by opening one or more radial incisions in the cornea 104 from the front of the eye 200, to reach the intracorneal channel 202. (In cases where there are two existing incisions, initially made during a prior keratopigmentation procedure, preferably both incisions are opened.) The radial incision(s) may be opened using an ophthalmological spatula.

Next, at Step 904, the blunt tip 402(a) of the irrigation device's cannula 400 is inserted into the intracorneal channel 202 via one of the opened radial incisions.

At Step 906, the blunt tip 402(a) of the cannula 400, previously referenced as 311(a) of the irrigation device 311, is moved or rotated within the intracorneal channel 202 back and forth. By moving or rotating the cannula within the intracorneal channel 202 back and forth, one scrubs and detaches the color pigments 203 from walls of the intracorneal channel 202.

At Step 908, either while scrubbing the walls of the intracorneal channel 202 or following the scrubbing step 906, an irrigation fluid (liquid) 304 is injected into the intracorneal channel 202 to flush out the detached color pigments from the intracorneal channel 202 via one or more opened radial incisions. In addition, any previously unattached pigment that might have been present in the intracorneal channel would also get flushed out. In one embodiment of the invention, the irrigation fluid is a balanced salt solution.

Figure 10A:
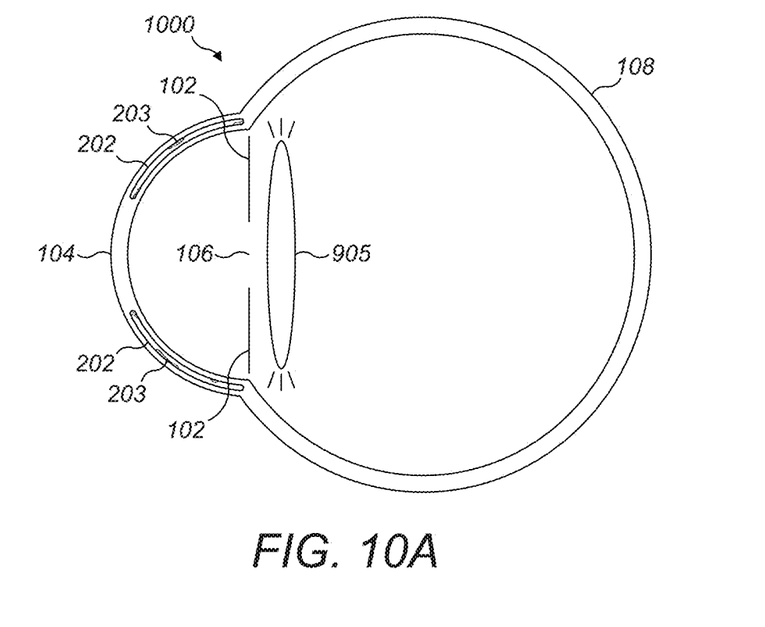
FIGS. 10A and 10B illustrate cross-sectional view and front view, respectively, of human eye after the depigmentation procedure of the present invention.
Figure 10B:
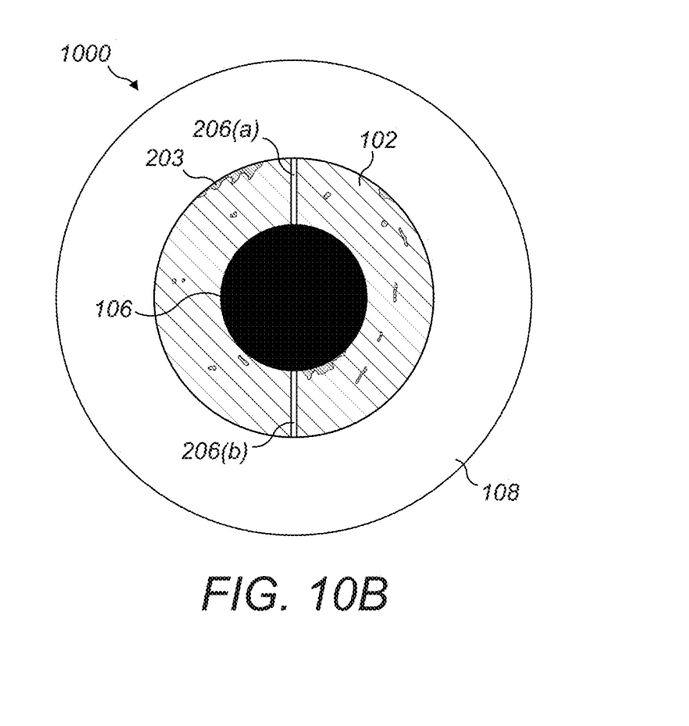

FIGS. 10A and 10B present a cross-sectional view and a front view respectively, of a human eye 200 after the invented depigmentation procedure. Specifically, FIG. 10A demonstrates that all or substantially all of the color pigments 203, previously deposited during a keratopigmentation procedure, have substantially been removed from the intracorneal channel 202.

FIG. 10B, for example, shows that the color pigment(s) 203 was substantially removed from the intracorneal channel 202. Moreover, FIG. 10B shows that the iris 102, previously masked by the color pigment 203, is now clearly visible, indicating that the visual impact of the previously performed keratopigmentation procedure was either fully or substantially reversed and the natural color of the eye was successfully restored.

While the foregoing descriptions may disclose specific values, unless expressly stated otherwise, other specific values may be used to achieve similar results. Further, the various features of the foregoing embodiments may be selected and combined to produce numerous variations of improved systems.

In the foregoing specification, exemplary embodiments have been described. However, one of ordinary skill in the art would appreciate that various modifications and changes can be made without departing from the scope of the invention as set forth in the claims below.

For example, a syringe may be replaced by a non-manual fluid-dispensing apparatus. The apparatus may be operated by a computer in response to operator's commands, e.g., voice commands. The pressure with which the irrigation fluid would flow could also be computer controlled.

The specification and figures are to be regarded in an illustrative rather than a restrictive sense, and all such modifications are intended to be included within the scope of present teachings, and therefore the scope of the invention is to be limited only by the claims.

Moreover, in this document, relational terms such as first and second, up and down, and the like may be used solely to distinguish one entity or action from another entity or action without necessarily requiring or implying any actual relationship or order between such entities or actions. The terms "comprise(s)", "comprising", "has", "having", "includes", "including", "contains", "containing" or any other variation thereof, are intended to cover a non-exclusive inclusion, so that a process, method, article, or apparatus that comprises, has, includes or contains a list of elements does not include only those elements but may include other elements not expressly listed or inherent to such process, method, article, or apparatus. An element preceded by "comprises . . . a". "has . . . a", "includes . . . a" or "contains . . . a" does not, without more constraints, preclude the existence of additional identical elements in the process, method, article, or apparatus that comprises, has, includes, or contains the element. The terms "a" and "an" are defined as one or more unless explicitly stated otherwise herein. The terms "substantially", "essentially", "approximately", "about" or any other version thereof, are defined as being close to as understood by one of ordinary skill in the art. The term "coupled" as used herein is defined as connected, although not necessarily directly. A device or structure that is "configured" in a certain way is configured in at least that way but may also be configured in ways that are not listed.

In addition, in the foregoing Detailed Description, various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

I claim:

1. A method for irrigating an intracorneal channel within a cornea using a hand-held irrigation device comprising a cannula that includes (i) a shaft section having a first end, (ii) an arcuate section having a blunt tip, wherein an exterior surface of the arcuate section comprises a rough-surface region, and (iii) a lumen extending from the first end of the shaft section toward the blunt tip of the arcuate section, the lumen including an opening in the rough-surface region of the arcuate section, the method comprising the steps of:
    accessing the intracorneal channel via a radial incision;
    inserting a part of the rough-surface region of the arcuate section into the intracorneal channel;
    moving the inserted part of the rough-surface region of the arcuate section within the intracorneal channel to detach a plurality of color pigments from a first wall of the intracorneal channel and a second wall of the intracorneal channel; and
    injecting an irrigation fluid into the intracorneal channel through the opening, to flush the detached plurality of color pigments from the intracorneal channel.

2. The method of claim 1, wherein the injecting step is performed by injecting the irrigating fluid into the intracorneal channel through the lumen opening in the rough-surface region of the arcuate section.

3. The method of claim 2, wherein the injecting step is performed simultaneously with the moving step.

4. The method of claim 2, wherein the injecting step is performed following the moving step.

5. The method of claim 1, wherein the moving step comprises moving the inserted part of the rough-surface region back and forth.

6. The method of claim 1, wherein the step of accessing the intracorneal channel via a radial incision is performed using a spatula.

* * * * *